US011100496B1

(12) United States Patent
Bavi et al.

(10) Patent No.: US 11,100,496 B1
(45) Date of Patent: Aug. 24, 2021

(54) ELECTRONIC SIGNATURE LEVERAGING FOR CONSOLIDATED TRANSACTIONS

(71) Applicant: CVS Pharmacy, Inc., Woonsocket, RI (US)

(72) Inventors: Subhash A. Bavi, Glendale, AZ (US); Dharmendra Gudimetla, Fountain Hills, AZ (US); Srinivas Loke, Naperville, IL (US)

(73) Assignee: CVS Pharmacy, Inc., Woonsocket, RI (US)

( * ) Notice: Subject to any disclaimer, the term of this patent is extended or adjusted under 35 U.S.C. 154(b) by 0 days.

(21) Appl. No.: 16/409,365

(22) Filed: May 10, 2019

(51) Int. Cl.
  *G06Q 20/38* (2012.01)
  *G06Q 20/40* (2012.01)
  *G06Q 30/06* (2012.01)

(52) U.S. Cl.
  CPC ....... *G06Q 20/3825* (2013.01); *G06Q 20/405* (2013.01); *G06Q 30/0635* (2013.01)

(58) Field of Classification Search
  CPC ............. G06Q 20/3825; G06Q 20/405; G06Q 30/0635
  See application file for complete search history.

(56) References Cited

U.S. PATENT DOCUMENTS

| | | | | |
|---|---|---|---|---|
| 8,504,383 | B1* | 8/2013 | Malley | G06Q 50/22 705/2 |
| 10,366,784 | B1* | 7/2019 | Eller | G16H 20/10 |
| 2009/0132943 | A1* | 5/2009 | Minsky | H04L 67/42 715/767 |
| 2012/0130888 | A1* | 5/2012 | Cooke | G06Q 20/3272 705/39 |
| 2012/0253852 | A1* | 10/2012 | Pourfallah | G06Q 20/3276 705/4 |
| 2013/0060575 | A1* | 3/2013 | Nee | G06Q 50/22 705/2 |
| 2013/0297333 | A1* | 11/2013 | Timmons | G06F 19/3456 705/2 |
| 2016/0189276 | A1* | 6/2016 | Batra | G06Q 30/0639 705/26.8 |
| 2018/0005235 | A1* | 1/2018 | Thorne | G06Q 20/3829 |
| 2018/0285860 | A1* | 10/2018 | Prabhu | G06Q 20/325 |

* cited by examiner

*Primary Examiner* — Scott C Anderson
(74) *Attorney, Agent, or Firm* — Patent Law Works LLP (57) ABSTRACT

An order completion system and method are described. In some implementations, the system may execute the method which includes receiving an order from a user that includes a retail component; determining that a profile identification (ID) of the user is associated with prescription information of the user; forming a consolidated order by adding one or more eligible prescriptions associated with the user to the retail component of the order using the prescription information. The method may further include applying transaction rules to the consolidated order to determine whether the consolidated order is eligible for a single input authorized checkout; and responsive to determining whether the consolidated order is eligible for the single input authorized checkout, presenting to the user via a user interface, a prompt for the user to complete the consolidated order using the single input authorized checkout.

20 Claims, 5 Drawing Sheets

ELECTRONIC SIGNATURE LEVERAGING FOR CONSOLIDATED TRANSACTIONS

BACKGROUND

Innovative vendors are constantly seeking ways to make purchasing fast, seamless and attractive to customers in order to maximize sales and profit. For example, some brick-and-mortar vendors sometimes provide in-aisle checkout, mobile payments, among other fast checkout solutions to shoppers. In the online space, a customer's stored data on file (e.g., stored credit card on a customer's record) may sometimes be used by vendors to auto-populate fields (e.g., billing and shipping fields on an online checkout form) following which the customer may be prompted to manually enter other verification data (e.g., a card verification value (CVV) code of the customer's card on file) in order to complete a purchase. In spite of these solutions, most customers still expect and generally adopt order completion technology that makes their purchasing experience fast and easy.

Existing solutions for completing transactions/orders in the wholesale and retail industries do not generally facilitate combining transactions originating from different industries/organizations much less leveraging a streamlined checkout solution for such transactions. Some of the problems faced by these existing solutions include innovatively retaining customer information (e.g., credit/debit cards, billing and shipping information, rewards data, pharmacy/prescription information, etc.) and appropriately leveraging/combining/applying this relevant customer information in completing transactions for customers, particularly when those transactions are directed to different departments/industries (e.g., pharmacy and retail orders), and must be combined into a single transaction for the customer before the customer checks out.

Further, certain transactions require customers to acknowledge/accept certain transactional terms (e.g., terms indicating that the customer understands how a particular prescription should be taken, disclaimers from a vendor regarding a product, etc.) by either manually or digitally signing documents in order to complete such transactions.

SUMMARY

A system for leveraging electronic signatures for consolidated order processing is described. Implementations of the system may perform the following operations: receiving, at a user device, an order from a user, the order including a retail component; determining that a profile identification (ID) of the user is associated with prescription information of the user; forming a consolidated order by adding to the retail component of the order, one or more eligible prescriptions associated with the user using the prescription information of the user; applying one or more transaction rules to the consolidated order to determine whether the consolidated order is eligible for a single input authorized checkout; and responsive to determining whether the consolidated order is eligible for the single input authorized checkout, presenting to the user via a user interface of the user device, a prompt for the user to complete the consolidated order using the single input authorized checkout.

Another general aspect includes a system comprising a processor and memory storing instructions that, when executed by the processor, cause the system to: receive, at a user device, an order from a user, the order including a retail component; determine that a profile identification (ID) of the user is associated with prescription information of the user; form a consolidated order by adding to the retail component of the order, one or more eligible prescriptions associated with the user using the prescription information of the user; apply one or more transaction rules to the consolidated order to determine whether the consolidated order is eligible for a single input authorized checkout; and responsive to determining whether the consolidated order is eligible for the single input authorized checkout, present to the user via a user interface of the user device, a prompt for the user to complete the consolidated order using the single input authorized checkout.

Implementations may include one or more of the following features. Although described in reference to a computer-implemented method, the features may also be applicable to operations performed by the system by executing instructions for the methods using a processor of the system. The computer-implemented method further comprising determining that a pre-existing electronic signature associated with the profile ID is authorized for prescription-based transactions; and applying the pre-existing electronic signature to confirm terms associated with the consolidated order, terms including specific transaction agreements associated with the consolidated order, the specific transaction agreements including agreements between the user and a vendor regarding guidelines associated with the one or more eligible prescriptions of the consolidated order. The computer-implemented method wherein determining that the pre-existing electronic signature associated with the profile ID is authorized for prescription-based transactions comprises determining that the one or more eligible prescriptions includes a drug from an approved drug class. The computer-implemented method wherein determining that the pre-existing electronic signature associated with the profile ID is authorized for prescription-based transactions comprises determining that the one or more eligible prescriptions include a drug from an approved drug group having a national drug code (NDC), the NDC being an identifier for human drugs. The computer-implemented method wherein determining that the pre-existing electronic signature associated with the profile ID is authorized for prescription-based transactions comprises determining that the one or more eligible prescriptions include a drug from an approved drug group, the approved drug group having a generic code number (GCN) representing a generic formulation of drugs. The computer-implemented method further comprising: determining that the one or more eligible prescriptions belongs to an authorized drug therapeutic class; and applying the pre-existing electronic signature to validate the terms associated with the consolidated order. The computer-implemented method wherein the transaction rules comprise: determining that one or more items within the retail component of the order is available to be ordered; verifying that a device ID associated with the user device is associated with the profile ID; evaluating the consolidated order relative to historical past orders associated with the profile ID to assess a likelihood of fraud; comparing an amount associated with the consolidated order to a threshold amount associated with the profile ID; assessing a percentage of historical order pickups associated with the profile ID relative to historical orders placed using the profile ID; and determining an eligible reward to apply to the consolidated order based on rewards data associated with the profile ID. The computer-implemented method further comprising: automatically applying payment information associated with the profile ID to pay for the consolidated order, the payment information including a flexible spending account (FSA) and a non-FSA, wherein costs associated with the consolidated order are automatically split between FSA eligible products within the consolidated order and non-FSA eligible products within the consolidated order; and wherein the prompt for the user to complete the consolidated order includes a summary of applied payment information to products associated with the retail component within the consolidated order, and products associated with the prescriptions within the consolidated order. The computer-implemented method wherein the pre-existing electronic signature of the user associated with the profile ID is a digital signature of the user, stored in association with the profile ID of the user.

Other implementations of one or more of these aspects include corresponding systems, apparatus, and computer programs, configured to perform the actions of the methods, encoded on computer storage devices.

It should be understood that the language used in the present disclosure has been principally selected for readability and instructional purposes, and not to limit the scope of the subject matter disclosed herein.

BRIEF DESCRIPTION OF THE DRAWINGS

The present disclosure is illustrated by way of example, and not by way of limitation in the figures of the accompanying drawings in which like reference numerals are used to refer to similar elements.

DETAILED DESCRIPTION

As set forth in detail below, the technology described herein provides an innovative approach to processing and completing orders. More specifically, the technology described herein may provide a system and method for leveraging electronic signatures during the fulfillment of mixed/consolidated orders (e.g., containing pharmacy items and retail items). For example, the technology described herein may determine information regarding prescription medications and, in some instances, retail items. The technology disclosed can further evaluate prescription-specific information, incorporate securely stored digital/electronic signatures of a customers to process order logistics in order to complete orders made by customers, and intelligently orchestrate fulfillment, and/or delivery of the prescription and/or retail items associated with the customers' orders.

The technology described herein can improve digital engagement of customers by providing an incentive for customers to use digital resources (e.g., stored customer digital signatures, specific computer systems and software, etc.) to easily and quickly place orders, automatically validate transactional terms and other conditions of agreement and/or disclosures using digital/electronic signatures of customers, and pay for medication and/or other retail items. Further, the digital tools allow the customer to perform these actions before visiting the store in order to provide an expedited pickup or delivery process.

It should be noted that although this specification refers to retail prescriptions, the technology described herein is also applicable to a pharmacy benefit manager (PBM) or third-party administrator of prescription drug programs, delivery (e.g., same day delivery) of mail order prescriptions via transfer to stores 112 or fulfillment centers, delivery (e.g., same day delivery) where the prescription may be put in the mail and retail items may be shipped separately from the store as part of the same order, etc.

These and other features may provide a substantially faster order placement experience for customers, secure authentication/validation of transaction documents (e.g., pharmacy disclosure agreements, etc.), reduced overall transaction time, increased digital engagement of the customer with products and services, and dynamically determined ordering and fulfillment processes based on factors, such as user preference, user behavior, type of medication, inventory, location of a store, etc.

With reference to the figures, reference numbers may be used to refer to components found in any of the figures, regardless of whether those reference numbers are shown in the figure being described. Further, where a reference number includes a letter referring to one of multiple similar components (e.g., component 000a, 000b, and 000n), the reference number may be used without the letter to refer to one or all of the similar components.

Figure 1:
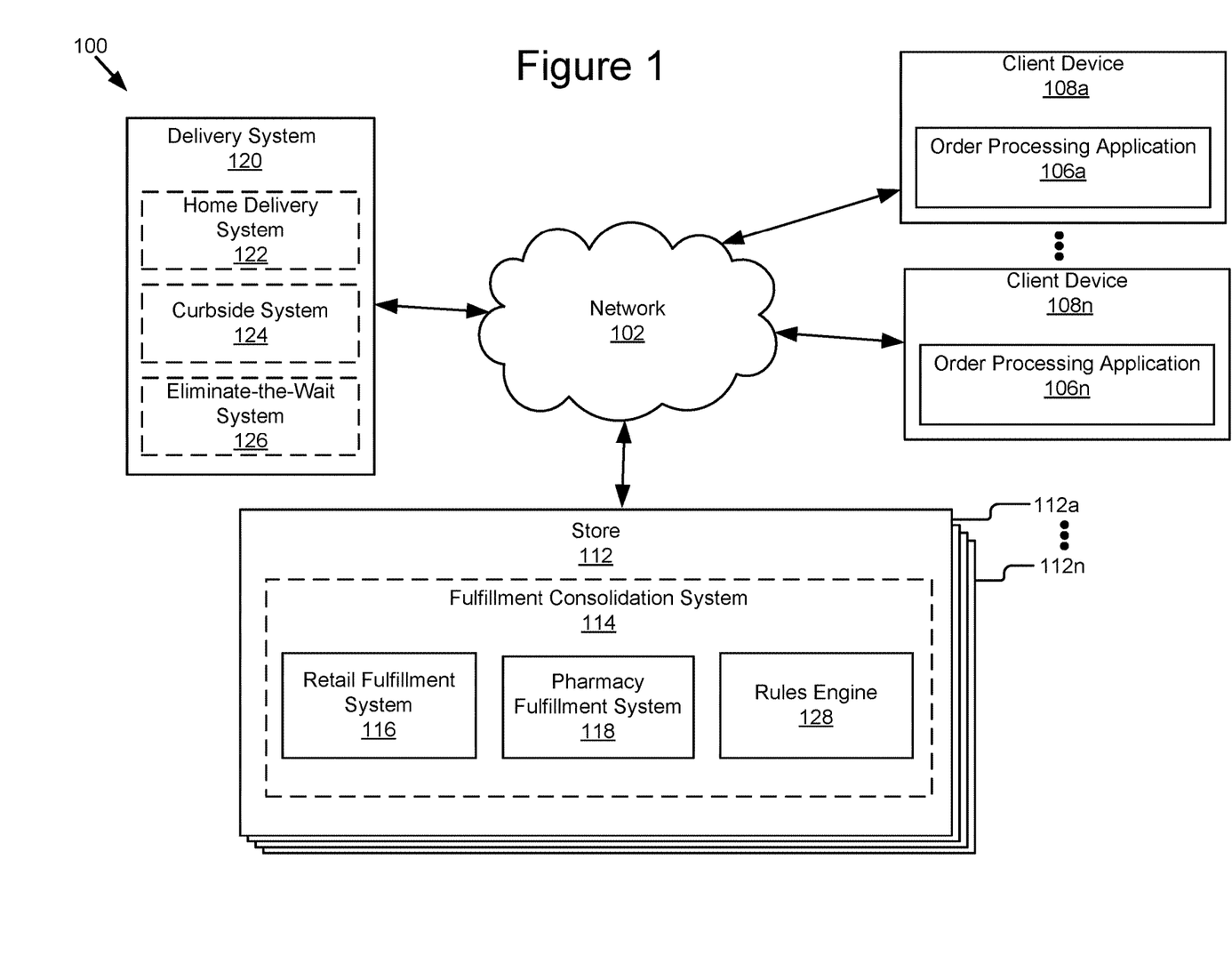
FIG. 1 is a high-level block diagram illustrating an example system in which a single input checkout for consolidated transactions may be implemented.

FIG. 1 is a high-level block diagram illustrating an example system in which a single input checkout for consolidated transactions/orders may be implemented. The illustrated system 100 may include one or more client devices 108a-108n, one or more stores 112a-112n, and a delivery system 120, which may be communicatively coupled via a network 102 for interaction with one another, although other system configurations are possible including other devices, systems, and networks. For example, the system 100 could include any number of client devices 108, stores 112, delivery systems 120, and other systems and devices (e.g., data store, etc.).

The network 102 may include any number of networks and/or network types. For example, the network 102 may include, but is not limited to, one or more local area networks (LANs), wide area networks (WANs) (e.g., the Internet), virtual private networks (VPNs), wireless wide area networks (WWANs), WiMAX® networks, personal area networks (PANs) (e.g., Bluetooth® communication networks), various combinations thereof, etc. These private and/or public networks may have any number of configurations and/or topologies, and data may be transmitted via the networks using a variety of different communication protocols including, for example, various Internet layer, transport layer, or application layer protocols. For example, data may be transmitted via the networks using TCP/IP, UDP, TCP, HTTP, HTTPS, DASH, RTSP, RTP, RTCP, VOIP, FTP, WS, WAP, SMS, MMS, XMS, IMAP, SMTP, POP, WebDAV, or other known protocols.

The client device 108 includes one or more computing devices having data processing and communication capabilities. The client device 108 may be coupled to communicate with other client devices and/or the other entities of the system 100 via the network 102 using a wireless and/or wired connection. Examples of client devices 108 may include, but are not limited to, mobile phones, smartphones, wearable smart devices (e.g., a smartwatch), tablets, laptops, desktops, netbooks, server appliances, servers, virtual machines, TVs, kiosks, in-vehicle computers (e.g., an automobile data or entertainment control system), etc. The system 100 may include any number of client devices 108, including client devices of the same or different type.

In some implementations, the client device 108 may include an order processing application 106. A user of the client device 108 may use the input/output devices of the client device 108 to interact with the order processing application 106 installed on the client device 108 or a browser, text messaging application, dedicated mobile application, push messaging service, etc., for interacting with the order processing application 106.

The order processing application 106 may include computer logic executable by a processor on a client device 108 or, in some implementations, a control server (not shown) associated with one or more vendors/merchants, to provide for user interaction, receive user input, present information to the user via a display, and send data to and receive data from other entities of the system 100, for example, via the network 102. In some implementations, the order processing application 106 may generate and present user interfaces based at least in part on information received from the merchant's control server and/or other data sources (e.g., data store, etc.). In some implementations, the order processing application 106 may be an application coupled to communicate with the delivery system 120. For example, the order processing application 106 may include a web browser and/or code operable therein, a customized client-side application (e.g., a dedicated application), a combination of both, etc. In some implementations, some or all of the components of the order processing application 106 are operable on the merchant's control server, and the client device 108 may access the functionality of the order processing application 106 using a web browser, text messaging application, or other application on the client device 108.

The order processing application 106 may include a pharmacy and/or retail/grocery application executable on a mobile device (e.g., a smartphone), a tablet, a laptop, or a desktop, or, in some implementations, the order processing application 106 may include a mobile, tablet, or desktop web application. The order processing application 106 may allow the user of the client device 108 to selectively combine one or more pharmacy and retail products into a digital cart, provide means (e.g., clickable icon or other visual indicator on a display device or an input device associated with the client device 108) to the user/customer to enter a single input checkout (e.g., one-click-checkout) for the products in the digital cart, and generate a record (e.g., receipt, barcode, etc.) for the checkout which can be used by the customer to receive ordered products, return ordered products, track ordered products, etc. In some embodiments, the order processing application 106 can send control signals to the fulfillment consolidation system 114 of the store 112 via the network 102 in order to process the fulfillment of products in the digital cart. This is further discussed elsewhere herein.

It should be understood that the functionality of the order processing application 106 may be distributed among one or more components of the system 100. While the descriptions herein include these and other procedures, it should be understood that the techniques apply to systems, such as a prescription management system and/or grocery management system, which may provide text and e-mail alerts, weekly or monthly statements or summaries, prescription benefit management, grocery rewards management, prescription savings or coupon management etc.

The store 112 may include one or more computing devices having data processing and communication capabilities. In some implementations, the store 112 may have a central computing device that communicates with its subsystems. In other implementations, one or more systems/component devices (e.g., 116, 118, and 128) of the store 112 may independently communicate with each other and with other components of the system 100 via the network 102.

The fulfillment consolidation system 114 may include one or more computing devices/systems for use in consolidating/combining retail items and pharmacy items. The fulfillment consolidation system 114 may include the retail fulfillment system 116, the pharmacy fulfillment system 118 and the rules engine 128. Examples of the systems 116 and 118 may include, but are not limited to, mobile phones, smartphones, mobile scanners, barcode scanners, wearable smart devices (e.g., a smartwatch), tablets, laptops, desktops, netbooks, server appliances, servers, virtual machines, TVs, kiosks, point of sale or register systems, etc.

The retail fulfillment system 116 may include one or more computing devices (e.g., as described above) for use in communicating with the order processing application 106 and facilitating fulfillment of retail items. For example, the retail fulfillment system 116 may receive instructions for fulfilling the retail component(s) of an order, such as which retail items are in the order (i.e., in the digital cart), attributes (e.g., size, number, etc.) of retail items, quantity of bags/packages in which to package the retail items, whether to deliver the retail items to the pharmacy or another location in the store 112 (or curbside, a freezer, a central drop off location, etc.), whether to refrigerate the retail items, when to retrieve, package, or deliver the items, whether the order also includes a pharmacy component, etc.

The pharmacy fulfillment system 118 may include one or more computing devices (e.g., as described above) for use in communicating with the order processing application 106 and facilitating fulfillment of pharmacy items (e.g., prescription medications, over the counter medications, and other pharmacy related items), as described in further detail elsewhere herein. For example, the pharmacy fulfillment system 118 may provide information for fulfilling the pharmacy component(s) of an order, such as identifying which pharmacy items (e.g., medication(s)) are in the order, attributes of the pharmacy items, authorization data (e.g., which individuals are authorized to pick up a prescription), whether to refrigerate the pharmacy items, whether/when to mix the pharmacy items, whether the order also includes a retail component, whether a customer has electronically/digitally signed for a prescription, whether to offer counseling to a customer, etc.

In some implementations the fulfillment consolidation system 114 can receive, using the retail fulfillment system 116 and/or the pharmacy fulfillment system 118, data (e.g., a digital token consisting of an encrypted profile ID of the user/customer, a device ID of the client device 108, etc.) responsive to the customer populating the digital cart discussed above with reference to the order processing application 106. The data received by the fulfillment consolidation system 114 can be processed and confirmed to determine what rules to apply to the customer's order and how to fulfill the customer's order. For example, the fulfillment consolidation system 114 may process the received data by decrypting a profile ID from a digital token associated with the customer, checking if the profile ID is tied to prescription based products, retrieving loyalty data associated with the customer, determining applicable coupons to apply to the customer's order, determining whether the profile ID has one or more prescriptions in a waiting bin that are eligible for pickup/pre-pay, retrieving the customer/user's profile based on the profile ID, and determining if the user profile has an associated securely stored digital/electronic signature that can be leveraged to complete the user's order, etc.

After processing the data, the fulfillment consolidation system 114 can engage the rules engine 128 for further processing of the processed data. For example, the rules engine 128 can be engaged by the fulfillment consolidation system 114 to retrieve past purchases during a specific time frame (e.g., X days, Y months, and Z years) made by the user/customer based on the user's profile ID and/or the device ID. In other embodiments, the rules engine 128 can be engaged to retrieve a past transaction count associated with a given profile ID. The rules engine can also a) determine the user's preferred delivery method, b) whether the securely stored digital signature is allowed for prescription-based orders/transactions, c) what fraud rules to apply to the order, etc. In some cases, the fraud rules may be executed using the rules engine by determining if the user's purchase history is within a threshold of historical purchases associated with the user's profile, whether there are any inconsistencies between the user's current order and past orders, etc., and recommending any corrective security actions associated with the order and/or the user profile.

In some implementations, the fulfillment consolidation system 114 may include a fulfillment application (not shown, also referred to herein as a pick and pack application) that may be installed on one or more of the devices 116, 118, and 128. The fulfillment application may allow a store associate (e.g., pharmacy associate, retail associate, cashier, fulfillment associate, delivery associate, etc.) to log in to the fulfillment application and receive information for fulfilling an order based on the associate's role/credentials. The fulfillment application may be the same application across the devices 116, 118, and 128, or may be customized for devices 116, 118 or 128 when an associate (e.g., delivery associate, fulfillment associate, retail associate, pharmacy associate, cashier, etc.) logs into said device.

It should be understood that the fulfillment consolidation system 114 can be directly coupled to a storage system (not shown) such as a data store, or coupled to the storage system via the network 102. In some implementation, the fulfillment consolidation system 114 can retrieve securely stored information (e.g., stored electronic signatures of customers, stored customer/user profile, stored customer transaction cards such as a flexible spending account (FSA) cards and non-FSA cards, etc.) from the data storage system and process the retrieved data as discussed above. For instance, responsive to retrieving an FSA and/or non-FSA card information from the data storage system, the fulfillment consolidation system 114 can automatically calculate appropriate discounts or charges to apply to the customer's consolidated order based on the retrieved FSA and/or non-FSA card data. The fulfillment consolidation system 114 can further create an order summary after processing retrieved data associated with the customer's order and store the order summary in the data storage system. In some instances, the order summary is sent back to the user for verification prior to the user using the single input checkout to complete the order. In other embodiments, the order summary is sent to both the user (e.g., as a record for tracking, receiving or returning products purchased by the user) and the data storage system after the user completes the order using the single input checkout. In some embodiments, the fulfillment consolidation system may use the order summary to fulfill the customer's order.

The technology described herein may further provide different options to receive the products (e.g., prescription medications, over the counter medications, and retail items) in the consolidated order through any one of multiple delivery methods. For example, the technology may allow the user to pick up their processed order (which may include both pharmacy and retail items) in the store; have the order delivered curbside to the user's vehicle; or have the order delivered to the user (e.g., at home) using a delivery service (e.g., transportation network system or company—Uber®, Lyft®, postal service, same day delivery service, etc.). The technology provides various security handoffs to track the possession of medications or other pharmacy items, such as controlled substances, certain medications, etc., as further discussed below with reference to the delivery system 120.

The delivery system 120 can host services such as a home delivery system 122, a curbside delivery system 124, and/or an eliminate-the-wait system 126, which may be individual and/or incorporated into the services provided by the fulfillment consolidation system 114. For example, the delivery system 120 may communicate with the fulfillment consolidation system 114 (e.g., via the network 102) to send and receive order information, instructions, notifications, statuses, tokens, verifications, etc.

The home delivery system 122, the curbside delivery system 124, and/or the eliminate-the-wait system 126 may be computing systems configured to provide delivery and/or fulfillment services for the store 112. For example, the home delivery system 122 may include a computing system for organizing and/or communicating with drivers of a home delivery service (e.g., Uber®, Lyft®, etc.); the curbside delivery system 124 may include a computing system for organizing and/or communicating with associates of a curbside delivery or fulfillment service; and the eliminate-the-wait system 126 may include a computing system for organizing and/or communicating with associates of the store 112.

It should be noted that although the store 112 is referred to herein as "store," it may include any physical premises for fulfilling orders, such as a fulfillment center, fulfillment facility, a drugstore, or other locations that may fulfill and/or sell retail items and/or pharmacy items. Additionally, it should be understood that the system 100 illustrated in FIG. 1 is representative of an example system and that a variety of different system environments and configurations are contemplated and are within the scope of the present disclosure. For instance, various operations and/or functionality may be moved from a server to a client, or vice versa; data may be consolidated into a single data store or further segmented into additional data stores and some implementations may include additional or fewer computing devices, services, and/or networks; and may implement various functionality client or server-side. Further, various entities of the system may be integrated into a single computing device or system or divided into additional computing devices or systems, etc.

Figure 2:
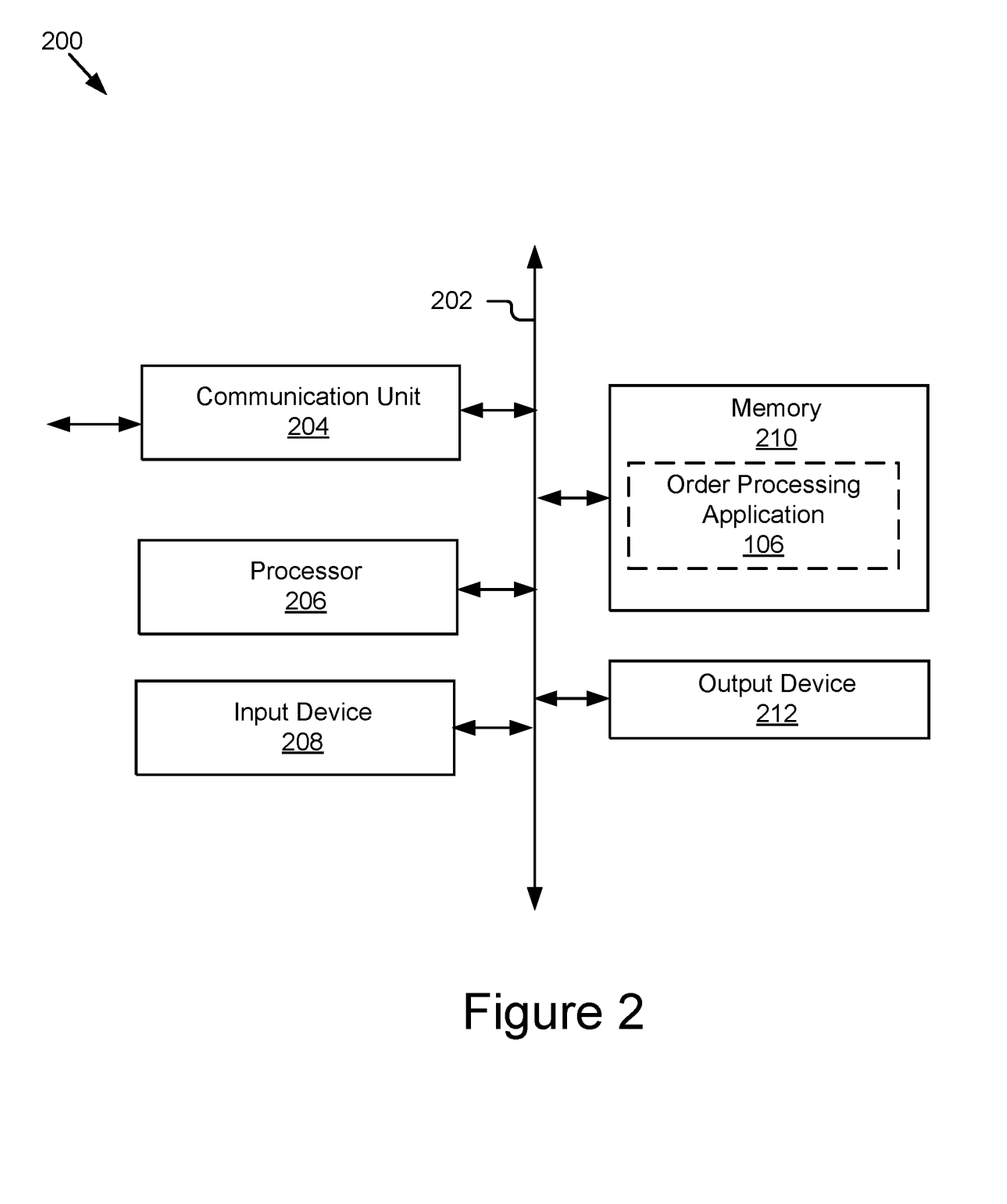
FIG. 2 is a block diagram illustrating an example computing system for executing applications associated with consolidated transactions.

FIG. 2 is a block diagram of an example computing device 200, which may represent the computer architecture of a client device 108 or the fulfillment consolidation system 114, or any other computing system described in FIG. 1, depending on the implementation. As depicted, the computing system 200 may include a communication unit 204, a processor 206, an input device 208, a memory 210, and an output device 212, which may be communicatively coupled by a communication bus 202. The computing system 200 depicted in FIG. 2 is provided by way of example and it should be understood that it may take other forms and include additional or fewer components without departing from the scope of the present disclosure. For instance, various components of the computing devices may be coupled for communication using a variety of communication protocols and/or technologies including, for instance, communication buses, software communication mechanisms, computer networks, etc. While not shown, the computing system 200 may include various operating systems, sensors, additional processors, and other physical configurations.

The processor 206 may execute software instructions by performing various input, logical, and/or mathematical operations. The processor 206 may have various computing architectures such as CISC, RISC, etc. The processor 206 may be physical and/or virtual and may include a single core or plurality of processing units and/or cores. In some implementations, the processor 206 may be coupled to the memory 210 via the bus 202 to access data and instructions therefrom and store data therein. The bus 202 may couple to the processor 206 and to the other components of the computing system 200 including, for example, the memory 210, the communication unit 204, the input device 208, and the output device 212.

The memory 210 may store and provide access to data and to other components of the computing system 200. The memory 210 may be included in a single computing device or a plurality of computing devices. In some implementations, the memory 210 may store instructions and/or data that may be executed by the processor 206. For example, the memory 210 may store one or more of the order processing application 106 that the processor 206 executes.

The order processing application 106 may include computer logic executable by the processor 206 to receive and process orders and may be accessible via one or more graphical user interfaces, as discussed elsewhere herein. The order processing application 106 may also be coupled to a data store (not shown) to store, retrieve, and/or manipulate data stored therein. In some implementations, the data store may be coupled to the computing system 200 via the network 102 and may provide securely stored data (e.g., customer profile, card information, shipping and billing information of customers, a user identifier, a prescription record identifier, user attributes, pharmacy item attributes, retail item attributes, store identification data, location data, etc.) to the Fulfillment consolidation system 114 and its subsystems.

The data store may include information sources for storing and providing access to data. In some implementations, the data store may store data associated with a database management system (DBMS) operable on the computing system 200. For example, the DBMS could include a structured query language (SQL) DBMS, a NoSQL DBMS, various combinations thereof, etc. In some instances, the DBMS may store data in multi-dimensional tables comprised of rows and columns, and manipulate, e.g., insert, query, update and/or delete, rows of data using programmatic operations.

It should be understood that the data store may be included in the computing system 200 or in another computing system and/or storage system distinct from but coupled to or accessible by the computing system 200. The data stores can include one or more non-transitory computer-readable mediums for storing data. In some implementations, the data stores may be incorporated with the memory or may be distinct therefrom.

In some implementations, the memory 210 may include one or more applications that execute the functionality of the fulfillment consolidation system 114 and its subsystems (i.e., the retail fulfillment system 116, the pharmacy fulfillment system 118, and the rules engine 128), depending on the configuration. The memory 210 can also store instructions that execute the functionality of the delivery system 120 and its subsystems (i.e., home delivery system 122, curbside delivery system 124, and eliminate-the-wait delivery system 126). The memory 210 is also capable of storing other instructions and data, including, for example, an operating system, hardware drivers, other software applications, databases, etc. The memory 210 may be coupled to the bus 202 for communication with the processor 206 and the other components of computing system 200.

The memory 210 may include a non-transitory computer-usable (e.g., readable, writeable, etc.) medium, which can be any non-transitory apparatus or device that can contain, store, communicate, propagate or transport instructions, data, computer programs, software, code, routines, etc., for processing by or in connection with the processor 206. In some implementations, the memory 210 may include one or more of volatile memory and non-volatile memory (e.g., RAM, ROM, hard disk, optical disk, etc.). It should be understood that the memory 210 may be a single device or may include multiple types of devices and configurations.

The bus 202 can include a communication bus for transferring data between components of a computing device or between computing devices, a network bus system including the network 102 or portions thereof, a processor mesh, a combination thereof, etc. In some implementations, the order processing application 106 and various other components operating on the computing device 200 (operating systems, device drivers, etc.) may cooperate and communicate via a communication mechanism included in or implemented in association with the bus 202. The software communication mechanism can include and/or facilitate, for example, inter-method communication, local function or procedure calls, remote procedure calls, an object broker (e.g., CORBA), direct socket communication (e.g., TCP/IP sockets) among software modules, UDP broadcasts and receipts, HTTP connections, etc. Further, any or all of the communication could be secure (e.g., SSH, HTTPS, etc.).

The communication unit 204 may include one or more interface devices (I/F) for wired and wireless connectivity among the components of the system 100. For instance, the communication unit 204 may include, but is not limited to, various types known connectivity and interface options. The communication unit 204 may be coupled to the other components of the computing system 200 via the bus 202. The communication unit 204 can provide other connections to the network 102 and to other entities of the system 100 using various standard communication protocols.

The input device 208 may include any device for inputting information into the computing system 200. In some implementations, the input device 208 may include one or more peripheral devices. For example, the input device 208 may include a keyboard, a pointing device, microphone, an image/video capture device (e.g., camera), a touch-screen display integrated with the output device 212, etc. The output device 212 may be any device capable of outputting information from the computing system 200. The output device 212 may include one or more of a display (LCD, OLED, etc.), a printer, a 3D printer, a haptic device, audio reproduction device, touch-screen display, a remote computing device, etc. In some implementations, the output device is a display which may display electronic images and data output by a processor of the computing system 200 for presentation to a user, such as the processor 206 or another dedicated processor.

Figure 3:
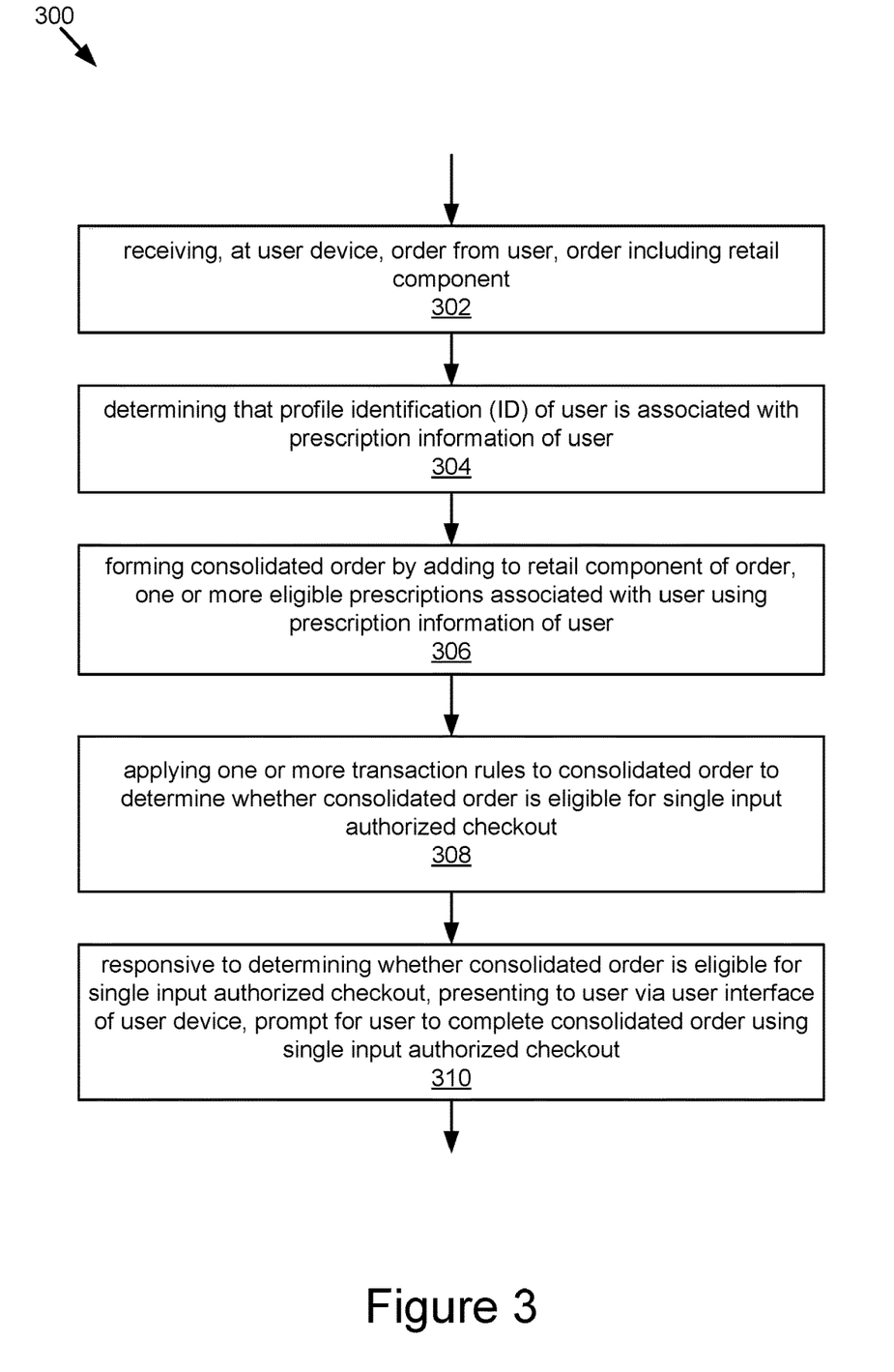
FIG. 3 is a flowchart of an example method for presenting a single input prompt to a user to complete a consolidated transaction.
Figure 4:
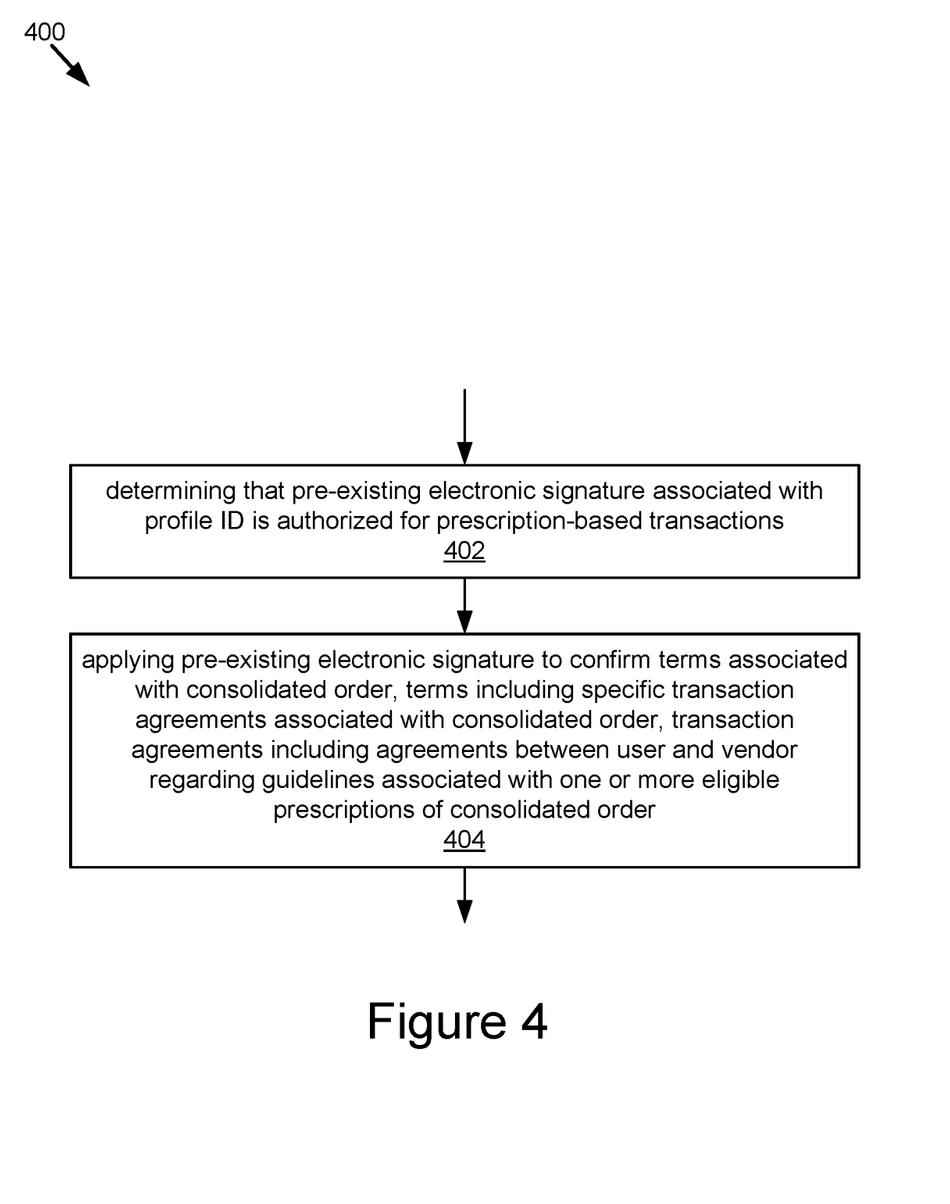
FIG. 4 is a flowchart of an example method for applying a pre-existing electronic signature to confirm terms associated with the consolidated order.
Figure 5:
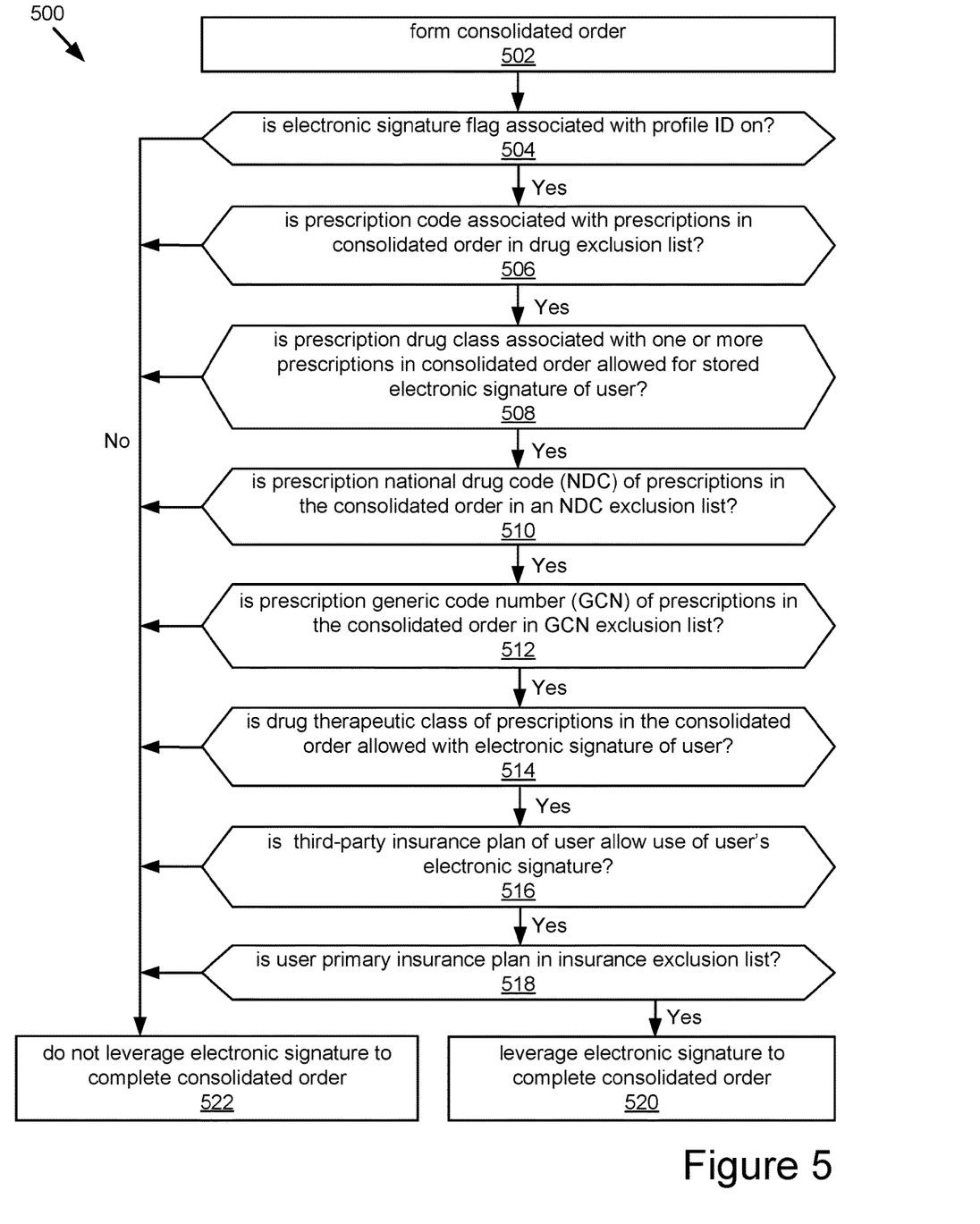
FIG. 5 is a flowchart of an example method for determining when to leverage an electronic signature of a customer to complete an order.

The methods described in FIGS. 3, 4, and 5 are illustrated as a collection of blocks in logical flow diagrams, which represent a sequence of operations, some or all of which can be implemented in hardware, software, or a combination thereof. The order in which the blocks are described should not be construed as a limitation. Any number of the described blocks can be combined in any order and/or in parallel to implement the methods, or alternative methods, and not all of the blocks need be executed. For ease of description, the methods are described with reference to the environments, architectures and systems described in the examples herein, although the methods may be implemented in a wide variety of other environments, architectures and systems.

FIG. 3 is a flowchart of an example method 300 for presenting a single input prompt to a user to complete a consolidated transaction. According to some implementations, the example method 300 includes receiving at 302, an order including a retail component from a user. For instance, the user may use the input device 208 of the client device 108 to select into a digital cart, products that may be from a pharmacy (i.e., medications, etc.) and/or from a retail store (e.g., groceries, etc.). In some instances, when the user populates the digital cart with one or more products including a retail component, the order processing application 106 may automatically transmit notifying signals to the fulfillment consolidation system 114. In other implementations, whenever the user populates the digital cart using the order processing application 106, the fulfillment consolidation system 114 receives a real-time notification with each update to the digital cart. The notifying signals that are sent to the fulfillment consolidation system 114 may include the profile identification (ID) of the user, the device ID of the client device, newly added items to the digital cart, etc.

The fulfillment consolidation system 114 may determine at 304, whether the profile ID of the user is associated with prescription information of the user. This is advantageous as it allows the system 100 to distinguish between customers having prescriptions and those that don't and to appropriately cater to the needs of customers/users that only purchase retail items and customers that purchase both pharmacy and retail products. At block 306, the fulfillment consolidation system 114 may form a consolidated order by adding to the retail component of the order, one or more eligible prescriptions associated with the user using the prescription information of the user. In some implementations, the user may already have prescriptions in waiting that are ready to be picked up and that may not necessarily be in the digital cart. The fulfillment consolidation system may automatically add such orders to the digital cart or optionally, transmit back to the client device 108, a notification about the prescriptions in waiting so the customer can accept/reject the addition of those prescriptions to the digital cart.

At block 308, the fulfillment consolidation system 114 may apply one or more transaction rules to the consolidated order to determine whether the consolidated order is eligible for a single input authorized checkout. The transaction rules may include determining whether the one or more items within the retail component of the order is available to be ordered, verifying that a device ID associated with the user device is associated with the profile ID, evaluating the consolidated order relative to historical past orders associated with the profile ID to assess a likelihood of fraud, comparing an amount associated with the consolidated order to a threshold amount associated with the profile ID, assessing a percentage of historical order pickups associated with the profile ID relative to historical orders placed using the profile ID, determining an eligible reward to apply to the consolidated order based on rewards data associated with the profile ID, etc.

At block 310, the fulfillment consolidation system 114 may present to the user via a user interface of the client device 106, a prompt for the user to complete the consolidated order using the single input authorized checkout. This may be in response to the fulfillment consolidation system 114 determining that the consolidated order is eligible for the single input authorized checkout. A single input authorized checkout may include an icon or some other visual indicator that can be interacted with (e.g., using a single click) by the user to, for example, pay for/checkout/place an order. Additionally, completing the order may include automatically using securely stored information about the user such as a pre-existing electronic signature of the user, the user's billing and shipping information on file, etc., without requiring the user to manually enter such information each time the user places orders at the store.

FIG. 4 is a flowchart of an example method 400 for applying a pre-existing electronic signature to confirm terms associated with the consolidated order. At block 402, the fulfillment consolidation system 114 may, as part of processing orders in the digital cart using the notification from the client device 108, determine that a pre-existing electronic signature associated with the profile ID is authorized for prescription-based transactions. As noted elsewhere herein, this pre-existing electronic signature may be securely stored in association with other information of the user such as billing information, insurance information, FSA cards, purchase history of the user, etc., on a data storage system. The fulfillment consolidation system 114 may also apply the pre-existing electronic signature to confirm terms associated with the consolidated order, the terms including specific transaction agreements associated with the consolidated order. The specific transaction agreements may include agreements between the user and a vendor regarding guidelines associated with the one or more eligible prescriptions of the consolidated order, etc. This is particularly advantageous, especially in situations where the user is ordering items that have been previously ordered before by the user, and which (i.e., the items) have specific transactional terms/agreements (e.g., disclosures/disclaimers/pharmacy instructions, etc., that the user has already read and knows) hence negating the need for the user to re-read such agreements. Thus, automatically applying the user's pre-existing electronic signature to validate/confirm/agree to such transactional terms can save a user, who is eligible for such a service, considerable amounts of time during the ordering process.

In some implementations, the fulfillment consolidation system 114 may, as part of determining that the pre-existing electronic signature associated with the profile ID is authorized for prescription-based transactions, determine that the one or more eligible prescriptions includes a drug from an approved drug class; determine that the one or more eligible prescriptions include a drug from an approved drug group having a national drug code (NDC) indicative of an identifier for human drugs; determine that the one or more eligible prescriptions include a drug from an approved drug group having a generic code number (GCN) representing a generic formulation of drugs; determine that the one or more eligible prescriptions belongs to an authorized drug therapeutic class, etc. Responsive to one or more of such determinations, the fulfillment consolidation system 114 may apply the pre-existing electronic signature to validate the terms associated with the consolidated order.

FIG. 5 is a flowchart of an example method 500 for determining when to leverage an electronic signature of a customer to complete an order. In executing the method 500, the fulfillment consolidation system 114 may, at block 502, form a consolidated order and test the consolidated order against the conditional logic shown in blocks 504-518 of FIG. 5.

At block 504, the fulfillment consolidation system 114 determines whether the electronic signature (also called pre-existing electronic/digital signature elsewhere herein) flag associated with the stored profile ID of the user is on. If this is the case, the fulfillment consolidation system can check, at 506, whether the prescription code associated with the prescriptions in the consolidated order are in a drug exclusion list. The drug exclusion list may include a drug list that a primary or secondary insurance intends to take out of user's coverage.

At block 508, the fulfillment consolidation system 114 determines whether the prescription drug class associated with one or more prescriptions in the consolidated order is allowed for the stored electronic signature of the user. The fulfillment consolidation system 114 can further determine: at block 510 whether the prescription NDC of prescriptions in the consolidated order are in an NDC exclusion list; at block 512 whether the prescription GCN of prescriptions in the consolidated order are in a GCN exclusion list; at block 514 whether the drug therapeutic class of prescriptions in the consolidated order are allowed with the electronic signature of the user; at block 516 whether the third-party insurance plan of the user allows using the user's electronic signature; at block 518 whether the user primary insurance plan is in an insurance exclusion list; etc. Responsive to such determinations, the fulfillment consolidation system 114 may either leverage (block 520) or not leverage (block 522) the electronic signature of the user in completing the consolidated order.

In the above description, for purposes of explanation, numerous specific details are set forth in order to provide a thorough understanding of the present disclosure. However, it should be understood that the technology described herein can be practiced without these specific details. Further, various systems, devices, and structures are shown in block diagram form in order to avoid obscuring the description. For instance, various implementations are described as having particular hardware, software, and user interfaces.

In some instances, various implementations may be presented herein in terms of algorithms and symbolic representations of operations on data bits within a computer memory. An algorithm is here, and generally, conceived to be a self-consistent set of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout this disclosure, discussions utilizing terms including "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Various implementations described herein may relate to an apparatus for performing the operations herein. This apparatus may be specially constructed for the required purposes, or it may comprise a general-purpose computer selectively activated or reconfigured by a computer program stored in the computer. Such a computer program may be stored in a computer-readable storage medium, including, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory or any type of media suitable for storing electronic instructions, each coupled to a computer system bus.

The technology described herein can take the form of an entirely hardware implementation, an entirely software implementation, or implementations containing both hardware and software elements. For instance, the technology may be implemented in software, which includes but is not limited to firmware, resident software, microcode, etc. Furthermore, the technology can take the form of a computer program object accessible from a computer-usable or computer-readable medium providing program code for use by or in connection with a computer or any instruction execution system. For the purposes of this description, a computer-usable or computer readable medium can be any non-transitory storage apparatus that can contain, store, communicate, propagate, or transport the program for use by or in connection with the instruction execution system, apparatus, or device.

A data processing system suitable for storing and/or executing program code may include at least one processor coupled directly or indirectly to memory elements through a system bus. The memory elements can include local memory employed during actual execution of the program code, bulk storage, and cache memories that provide temporary storage of at least some program code in order to reduce the number of times code must be retrieved from bulk storage during execution. Input or I/O devices (including but not limited to keyboards, displays, pointing devices, etc.) can be coupled to the system either directly or through intervening I/O controllers.

Network adapters may also be coupled to the system to enable the data processing system to become coupled to other data processing systems, storage devices, remote printers, etc., through intervening private and/or public networks. Wireless (e.g., Wi-Fi™) transceivers, ethernet adapters, and modems are just a few examples of network adapters. The private and public networks may have any number of configurations and/or topologies. Data may be transmitted between these devices via the networks using a variety of different communication protocols including, for example, various Internet layer, transport layer, or application layer protocols. For example, data may be transmitted via the networks using transmission control protocol/Internet protocol (TCP/IP), user datagram protocol (UDP), transmission control protocol (TCP), hypertext transfer protocol (HTTP), secure hypertext transfer protocol (HTTPS), dynamic adaptive streaming over HTTP (DASH), real-time streaming protocol (RTSP), real-time transport protocol (RTP) and the real-time transport control protocol (RTCP), voice over Internet protocol (VOIP), file transfer protocol (FTP), WebSocket (WS), wireless access protocol (WAP), various messaging protocols (SMS, MMS, XMS, IMAP, SMTP, POP, WebDAV, etc.), or other known protocols.

Finally, the structure, algorithms, and/or interfaces presented herein are not inherently related to any particular computer or other apparatus. Various general-purpose systems may be used with programs in accordance with the teachings herein, or it may prove convenient to construct more specialized apparatus to perform the required method blocks. The required structure for a variety of these systems will appear from the description above. In addition, the specification is not described with reference to any particular programming language. It will be appreciated that a variety of programming languages may be used to implement the teachings of the specification as described herein.

The foregoing description has been presented for the purposes of illustration and description. It is not intended to be exhaustive or to limit the specification to the precise form disclosed. Many modifications and variations are possible in light of the above teaching. As will be understood by those familiar with the art, the specification may be embodied in other specific forms without departing from the spirit or essential characteristics thereof. Likewise, the particular naming and division of the modules, routines, features, attributes, methodologies and other aspects are not mandatory or significant, and the mechanisms that implement the specification or its features may have different names, divisions and/or formats.

Furthermore, the modules, routines, features, attributes, methodologies and other aspects of the disclosure can be implemented as software, hardware, firmware, or any combination of the foregoing. Also, wherever a component, an example of which is a module, of the specification is implemented as software, the component can be implemented as a standalone program, as part of a larger program, as a plurality of separate programs, as a statically or dynamically linked library, as a kernel loadable module, as a device driver, and/or in every and any other way known now or in the future. Additionally, the disclosure is in no way limited to implementation in any specific programming language, or for any specific operating system or environment.

What is claimed is:

1. A computer-implemented method comprising:
  receiving, at a user device, an order from a user, the order including a retail component offered by a store;
  determining that a profile identification (ID) of the user is associated with prescription information of the user;
  determining that a pre-existing electronic signature associated with the profile ID authorizes adding prescription-based transactions offered by the store to the order of the retail component;
  forming a consolidated order in a digital cart in a user interface by adding to the retail component of the order, one or more eligible prescriptions associated with the user using the prescription information of the user;
  applying one or more transaction rules to the consolidated order to determine whether the consolidated order is eligible for a single input authorized checkout;
  responsive to determining the consolidated order is eligible for the single input authorized checkout, presenting to the user via the user interface of the user device, a single input visual icon to prompt the user to complete a purchase of the consolidated order using the single input authorized checkout of the consolidated order in the digital cart in the user interface; and
  responsive to the user selecting the single input visual icon with a single click on the single input visual icon in the user interface of the user device, performing all of applying the pre-existing electronic signature to validate terms associated with the consolidated order, and completing the purchase with the store of the consolidated order including the retail component and the one or more eligible prescriptions associated with the user.

2. The computer-implemented method of claim 1 further comprising:
  applying the pre-existing electronic signature to confirm terms associated with the consolidated order, the terms including specific transaction agreements associated with the consolidated order, the specific transaction agreements including agreements between the user and a vendor regarding guidelines associated with the one or more eligible prescriptions of the consolidated order.

3. The computer-implemented method of claim 2, wherein determining that the pre-existing electronic signature associated with the profile ID is authorized for prescription-based transactions comprises determining that the one or more eligible prescriptions includes a drug from an approved drug class.

4. The computer-implemented method of claim 2, wherein determining that the pre-existing electronic signature associated with the profile ID is authorized for prescription-based transactions comprises determining that the one or more eligible prescriptions include a drug from an approved drug group having a national drug code (NDC), the NDC being an identifier for human drugs.

5. The computer-implemented method of claim 2, wherein determining that the pre-existing electronic signature associated with the profile ID is authorized for prescription-based transactions comprises determining that the one or more eligible prescriptions include a drug from an approved drug group, the approved drug group having a generic code number (GCN) representing a generic formulation of drugs.

6. The computer-implemented method of claim 2, further comprising:
  determining that the one or more eligible prescriptions belongs to an authorized drug therapeutic class; and
  applying the pre-existing electronic signature to validate the terms associated with the consolidated order.

7. The computer-implemented method of claim 2, wherein the pre-existing electronic signature of the user associated with the profile ID is a digital signature of the user, stored in association with the profile ID of the user.

8. The computer-implemented method of claim 1, wherein the transaction rules comprise:
  determining that one or more items within the retail component of the order is available to be ordered; and
  verifying that a device ID associated with the user device is associated with the profile ID.

9. The computer-implemented method of claim 1, wherein the transaction rules comprise:
  evaluating the consolidated order relative to historical past orders associated with the profile ID to assess a likelihood of fraud;

comparing an amount associated with the consolidated order to a threshold amount associated with the profile ID;

assessing a percentage of historical order pickups associated with the profile ID relative to historical orders placed using the profile ID; and determining an eligible reward to apply to the consolidated order based on rewards data associated with the profile ID.

10. The computer-implemented method of claim 1, further comprising:

automatically applying payment information associated with the profile ID to pay for the consolidated order, the payment information including a flexible spending account (FSA) and a non-FSA, wherein costs associated with the consolidated order are automatically split between FSA eligible products within the consolidated order and non-FSA eligible products within the consolidated order; and wherein the prompt for the user to complete the purchase of the consolidated order includes a summary of applied payment information to products associated with the retail component within the consolidated order and products associated with the prescriptions within the consolidated order.

11. A system comprising:

a processor; and memory storing instructions that, when executed by the processor, cause the system to:

receive, at a user device, an order from a user, the order including a retail component offered by a store;

determine that a profile identification (ID) of the user is associated with prescription information of the user;

determine that a pre-existing electronic signature associated with the profile ID authorizes adding prescription-based transactions offered by the store to the order of the retail component;

form a consolidated order in a digital cart in a user interface by adding to the retail component of the order, one or more eligible prescriptions associated with the user using the prescription information of the user;

apply one or more transaction rules to the consolidated order to determine whether the consolidated order is eligible for a single input authorized checkout;

responsive to determining the consolidated order is eligible for the single input authorized checkout, present to the user via the user interface of the user device, a single input visual icon to prompt the user to complete a purchase of the consolidated order using the single input authorized checkout of the consolidated order in the digital cart in the user interface; and responsive to the user selecting the single input visual icon with a single click on the single input visual icon in the user interface of the user device, performing all of apply the pre-existing electronic signature to validate terms associated with the consolidated order, and completing the purchase with the store of the consolidated order including the retail component and the one or more eligible prescriptions associated with the user.

12. The system of claim 11, wherein the instructions are further executable by the processor to:

apply the pre-existing electronic signature to confirm terms associated with the consolidated order, the terms including specific transaction agreements associated with the consolidated order, the specific transaction agreements including agreements between the user and a vendor to follow guidelines associated with the one or more eligible prescriptions of the consolidated order.

13. The system of claim 12, wherein to determine that the pre-existing electronic signature associated with the profile ID is authorized for prescription-based transactions comprises determining that the one or more eligible prescriptions includes a drug from an approved drug class.

14. The system of claim 12, wherein to determine that the pre-existing electronic signature associated with the profile ID is authorized for prescription-based transactions comprises determining that the one or more eligible prescriptions include a drug from an approved drug group having a national drug code (NDC), the NDC being an identifier for human drugs.

15. The system of claim 12, wherein to determine that the pre-existing electronic signature associated with the profile ID is authorized for prescription-based transactions comprises determining that the one or more eligible prescriptions include a drug from an approved drug group, the approved drug group having a generic code number (GCN) representing a generic formulation of drugs.

16. The system of claim 12, wherein the instructions are further executable by the processor to:

determine that the one or more eligible prescriptions belongs to an authorized drug therapeutic class; and apply the pre-existing electronic signature to validate the terms associated with the consolidated order.

17. The system of claim 12, wherein the pre-existing electronic signature of the user associated with the profile ID is a digital signature of the user, stored in association with the profile ID of the user.

18. The system of claim 11, wherein the instructions are further executable by the processor to:

evaluate the consolidated order relative to historical past orders associated with the profile ID to assess a likelihood of fraud;

compare an amount associated with the consolidated order to a threshold amount associated with the profile ID;

assess a percentage of historical order pickups associated with the profile ID relative to historical orders placed using the profile ID; and determine an eligible reward to apply to the consolidated order based on rewards data associated with the profile ID.

19. The system of claim 11, wherein the instructions are further executable by the processor to:

automatically apply payment information associated with the profile ID to pay for the consolidated order, the payment information including a flexible spending account (FSA) and a non-FSA, wherein costs associated with the consolidated order are automatically split between FSA eligible products within the consolidated order and non-FSA eligible products within the consolidated order; and wherein the prompt for the user to complete the purchase of the consolidated order includes a summary of applied payment information to products associated with the retail component within the consolidated order and products associated with the prescriptions within the consolidated order.

20. A method comprising:

receiving, at a user device, an order from a user, the order including a retail component offered by a store;

determining that a profile identification (ID) of the user is associated with prescription information of the user;

determining that a pre-existing electronic signature associated with the profile ID authorizes adding prescription-based transactions offered by the store to the order of the retail component;

forming a consolidated order in a digital cart in a user interface by adding to the retail component of the order, one or more eligible prescriptions associated with the user using the prescription information of the user;

determining that a pre-existing electronic signature associated with the profile ID is authorized for completing the consolidated order;

applying the pre-existing electronic signature to confirm terms associated with the consolidated order, the terms including specific transaction agreements associated with the consolidated order, the specific transaction agreements including agreements between the user and a vendor regarding guidelines associated with the one or more eligible prescriptions of the consolidated order;

applying one or more transaction rules to the consolidated order to determine whether the consolidated order is eligible for a single input authorized checkout;

responsive to determining the consolidated order is eligible for the single input authorized checkout, presenting to the user via the user interface of the user device, a single input visual icon to prompt the user to complete a purchase of the consolidated order using the single input authorized checkout of the consolidated order in the digital cart in the user interface; and responsive to the user selecting the single input visual icon with a single click on the single input visual icon in the user interface of the user device, performing all of applying the pre-existing electronic signature to validate terms associated with the consolidated order, and completing the purchase with the store of the consolidated order including the retail component and the one or more eligible prescriptions associated with the user.

\* \* \* \* \*